US012766180B2

(12) United States Patent
Wang

(10) Patent No.: US 12,766,180 B2
(45) Date of Patent: Oct. 20, 2026

(54) FAGOPYRUM NUTRACEUTICAL COMPOSITIONS

(71) Applicant: DST Pharma, Inc., Duluth, GA (US)

(72) Inventor: Lu Wang, Duluth, GA (US)

(73) Assignee: DST Pharma, Inc., Duluth, GA (US)

( * ) Notice: Subject to any disclaimer, the term of this patent is extended or adjusted under 35 U.S.C. 154(b) by 121 days.

(21) Appl. No.: 18/603,823

(22) Filed: Mar. 13, 2024

(65) Prior Publication Data

US 2024/0307473 A1 Sep. 19, 2024

Related U.S. Application Data

(60) Continuation of application No. 17/931,368, filed on Sep. 12, 2022, now abandoned, which is a division of application No. 16/970,878, filed as application No. PCT/US2019/021549 on Mar. 11, 2019, now abandoned.

(60) Provisional application No. 62/756,287, filed on Nov. 6, 2018, provisional application No. 62/642,264, filed on Mar. 13, 2018.

(51) Int. Cl.

| | |
|---|---|
| ***A61K 36/70*** | (2006.01) |
| ***A23L 33/105*** | (2016.01) |
| ***A61K 31/353*** | (2006.01) |
| ***A61K 36/076*** | (2006.01) |
| ***A61K 36/28*** | (2006.01) |
| ***A61K 36/282*** | (2006.01) |
| ***A61K 36/288*** | (2006.01) |
| ***A61K 36/31*** | (2006.01) |
| ***A61K 36/36*** | (2006.01) |
| ***A61K 36/48*** | (2006.01) |
| ***A61K 36/536*** | (2006.01) |
| ***A61K 36/68*** | (2006.01) |
| ***A61K 36/82*** | (2006.01) |
| ***A61K 45/06*** | (2006.01) |
| ***A61P 31/14*** | (2006.01) |

(52) U.S. Cl.

CPC ............ *A61K 36/70* (2013.01); *A23L 33/105* (2016.08); *A61K 31/353* (2013.01); *A61K 36/076* (2013.01); *A61K 36/28* (2013.01); *A61K 36/282* (2013.01); *A61K 36/288* (2013.01); *A61K 36/31* (2013.01); *A61K 36/36* (2013.01); *A61K 36/48* (2013.01); *A61K 36/536* (2013.01); *A61K 36/68* (2013.01); *A61K 36/82* (2013.01); *A61K 45/06* (2013.01); *A61P 31/14* (2018.01); *A23V 2002/00* (2013.01)

(58) Field of Classification Search

None

See application file for complete search history.

(56) References Cited

U.S. PATENT DOCUMENTS 5,013,556 A 5/1991 Woodle et al.

FOREIGN PATENT DOCUMENTS

| | | |
|---|---|---|
| CN | 1362249 A | 8/2002 |
| CN | 102114227 A | 7/2011 |
| CN | 102755393 A | 10/2012 |
| CN | 106636288 A | 5/2017 |

OTHER PUBLICATIONS

CN 101632722 A (English translation)—2012.*

Li (Antiviral Chemistry Et Chemotherapy (2010), vol. 20, pp. 239-248).*

Jing et al., "Phytochemical and Pharmacological Profiles of Three Fagopyrum Buckwheats" Int J Mol Sci. Apr. 19, 2016; 17(4):589.

El-Serag, "Epidemiology of viral hepatitis and hepatocellular carcinoma" Gastroenterology. May 2012;142(6):1264-1273.e1.

Davis et al., "Interferon alfa-2b alone or in combination with ribavirin for the treatment of relapse of chronic hepatitis C. International Hepatitis Interventional Therapy Group" N Engl J Med. Nov. 9, 1998;339(21):1493-9.

Li Anjen, et al., "Polygonaceae," Flora of China, 5:277-350 (2003).

Swain et al., "A sustained virologic response is durable in patients with chronic hepatitis C treated with peginterferon alfa-2a and ribavirin." Gastroenterology. Nov. 2010;139(5):1593-601.

Sarrazin & Zeuzem "Resistance to direct antiviral agents in patients with hepatitis C virus infection" Gastroenterology. Feb. 2010; 138(2):447-62.

Chan, "Inhibition of tumor growth in vitro by the extract of fagopyrum cymosum (fago-c)" Life Sci. Mar. 7, 2003;72(16):1851-8.

* cited by examiner

*Primary Examiner* — Susan Hoffman

(74) *Attorney, Agent, or Firm* — Lisa Mueller; Tristan A. Fuierer; Casimir Jones SC

(57) ABSTRACT

*Fagopyrum dibotyo* nutraceuticals and methods of their use are provided. The disclosed *F. dibotyo* nutraceuticals are useful to improve or increase liver function and to treat liver diseases, especially those caused by viral hepatitis. In some embodiments, the *F. dibotyo* nutraceuticals also contain supplementary botanical extracts to confer additional health benefits.

6 Claims, 6 Drawing Sheets

Specification includes a Sequence Listing.

SEQUENCE LISTING

```
Sequence total quantity: 2
SEQ ID NO: 1            moltype = DNA  length = 19
FEATURE                 Location/Qualifiers
misc_feature            1..19
                        note = Synthetic
```

-continued

```
source                  1..19
                        mol_type = other DNA
                        organism = synthetic construct
SEQUENCE: 1
tcgtatgata cccgatgct                                        19

SEQ ID NO: 2            moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 2
gtttgaccct tgctgttga                                        19
```

FAGOPYRUM NUTRACEUTICAL COMPOSITIONS

CROSS-REFERENCE TO RELATED APPLICATIONS

This application is a continuation of U.S. patent application Ser. No. 17/931,368, filed Sep. 12, 2022, now abandoned, which is a division of U.S. patent application Ser. No. 16/970,878, filed Aug. 18, 2020, now abandoned, which is a national stage application under 35 U.S.C. § 371 of PCT/US2019/021549 filed Mar. 11, 2019, which claims benefit of and priority to U.S. Provisional Patent Application No. 62/642,264 filed Mar. 13, 2018, and U.S. Provisional Patent Application No. 62/756,287 filed on Nov. 6, 2018, all of which are incorporated by reference in their entirety.

REFERENCE TO SEQUENCE LISTING

Incorporated by reference in its entirety herein is a computer-readable nucleotide/amino acid sequence listing submitted concurrently herewith and identified as follows: One 3,386 Byte xml file named "DSTPH-38860-404-ST26.xml," created on Sep. 12, 2022.

FIELD OF THE INVENTION

The invention is generally related to nutraceutical compositions and their use to enhance or improve liver function.

BACKGROUND OF THE INVENTION

Hepatitis is an inflammation of the liver caused by hepatitis virus and other infections, toxic substances like alcohol and drugs, and autoimmune diseases. There are five main hepatitis viruses, hepatitis A virus (HAV), hepatitis B virus (HBV), hepatitis C virus (HCV), hepatitis D virus (HDV), and hepatitis E virus (HEV). HAV and HEV cause acute hepatitis, while HBV, HCV, and HDV are the cause of chronic hepatitis. Chronic infection with hepatitis can lead to chronic liver disease, cirrhosis, and hepatocellular carcinoma if left untreated (El-Serag, *Gastro.,* 142:1264-1273 (2012)). HBV and HCV are responsible for 96% of mortality from viral hepatitis. In 2015, viral hepatitis was estimated to have caused 1.34 million deaths worldwide, which is a 22% increase since 2000.

In 2015, it was estimated that 257 million people globally were living with chronic HBV and 71 million people were living with chronic HCV. Scaling up of the HBV vaccine has dramatically reduced the incidence of new HBV infections among children, however no such vaccination exists for HCV. The global burden of HCV has increased with nearly 1.75 million people acquiring HCV each year (WHO, Global Hepatitis Report (2017)).

The most commonly prescribed treatment for HCV is pegylated-IFN and ribavirin (PEG-IFN/RBV) (Davis, et al., *NEJM,* 339:1493-1499 (1998); Swain et al., *Gastro,* 139: 1593-1601 (2010)). While this treatment is effective at reducing viral load, it has multiple limitations and side effects. The antiviral activity of PEG-IFN/RBV is dependent on the host and viral genotype meaning it is not effective for some patients. In addition the safety and tolerability risk outweigh the treatment benefit in some patients. The treatment is also expensive, being unaffordable to many patients especially in developing countries where there is a high burden of the disease. While PEG-IFN/RBV is still the standard of care for some patients, a new class of drugs for HCV has emerged in the past decade. Direct acting antiviral (DAA) agents target different stages of the viral lifecycle of HCV. DAAs are often administered in combination with PEG-IFN/RBV. This combination therapy is highly effective at treating HCV and reducing viral load but increases the toxicity of both drugs. In addition, many patients taking DAAs acquire resistance to the drug, making them ineffective over time (Sarrazin and Zeuzem, *Gastro.,* 138:447-462 (2010)). While many of the current treatments for HCV are effective at reducing viral load, the safety and tolerability risks and price of treatment outweigh the benefits. There is still a need for new and effective treatments for HCV.

Therefore, it is an object of the invention to provide nutraceutical compositions and methods of their use to improve liver function.

It is also an object of the invention to provide nutraceutical compositions and methods of their use in treating liver diseases and disorders.

SUMMARY OF THE INVENTION

Nutraceutical compositions and methods of their use in treating viruses of the liver are provided. One embodiment provides a nutraceutical composition including an amount of *Fagopyrum dibotyo* extract effective to inhibit viruses that affect the liver. Another embodiment provides a nutraceutical composition for inhibiting viruses that affect the liver including 0.1 mg to 10 g of *Fagopyrum dibotyo* extract, and optionally an excipient. Exemplary viruses of the liver that can be treated include, but are not limited to hepatitis A, hepatitis B, or hepatitis C.

Another embodiment provides a nutraceutical composition for inhibiting viruses that affect the liver including 0.001% to 50% of 5,7,3',4'-tetrahydroxyflavan-3-ol $C_4$-$C_8$ dimers. The nutraceutical composition can also include 0.001% to about 50% of derivatives of 5,7,3',4'-tetrahydroxyflavan-3-ol $C_4$-$C_8$ dimers.

Still another embodiment provides a nutraceutical composition including 0.001% to about 50% of 5,7,3',4'-tetrahydroxyflavan-3-ol $C_4$-$C_8$ dimers in combination with other herbal compounds, extracts, or molecules. The herbal compounds can be green tea extract, milk thistle extract, *Semen cassiae* extract, *Spica prunellae* extract, Haike sapogenin, or a combination thereof.

The nutraceutical compositions can also include an anti-inflammatory medication, a diuretic, an anti-cancer medication, or combinations thereof. For example, the nutraceutical composition can include one or more compounds or extracts from *Plantago depressa* Wild., *Taraxacum mongolicum* Hand-Mazz., radix, forsythia, *Thlaspi arvense* Linn, *Artemisia capillaris* Thunb, Tai zi shen, or poria, or a combination thereof. The nutraceutical compositions are typically formulated for oral administration.

One embodiment provides a method of inhibiting viral hepatitis in a subject in need thereof by administering to the subject an effective amount of the disclosed nutraceutical compositions. The viral hepatitis can be hepatitis A, hepatitis B, or hepatitis C. The hepatitis can be late-stage hepatitis. The subject can be administered a second therapeutic for viral hepatitis.

Still another embodiment provides a method of improving or enhancing liver function in a subject in need thereof by administering to the subject an effective amount of a nutraceutical composition. In certain embodiments the nutraceutical composition includes 0.1 mg to 10 g *Fagopyrum dibotyo* extract or 0.001% to 50% of 5,7,3',4'-tetrahydroxyflavan-3-ol $C_4$-$C_8$ dimers.

Yet another embodiment provides a method of treating liver disease in a subject in need thereof by administering to the subject by administering to the subject an effective amount of *Fagopyrum dibotyo* extract to improve or enhance liver function in the subject. Another embodiment provides a method of treating liver disease in a subject in need thereof by administering to the subject a nutraceutical composition including 0.1 mg to 10 g *Fagopyrum dibotyo* extract or 0.001% to 50% of 5,7,3',4'-tetrahydroxyflavan-3-ol $C_4$-$C_8$ dimers. Preferably the subject is human. The nutraceutical composition is typically administered to the subject in need thereof until liver conditions improve.

Improvement in liver function or liver conditions can be measured by any one of symptoms of ascites, serum levels of liver enzymes including ALT, AST, ALP or γGT levels, liver fibrosis, or liver cirrhosis. In one embodiment, the liver condition is hepatitis A virus infection, hepatitis B virus infection, or hepatitis C virus infection.

DETAILED DESCRIPTION OF THE INVENTION

I. Definitions

Figure 1:
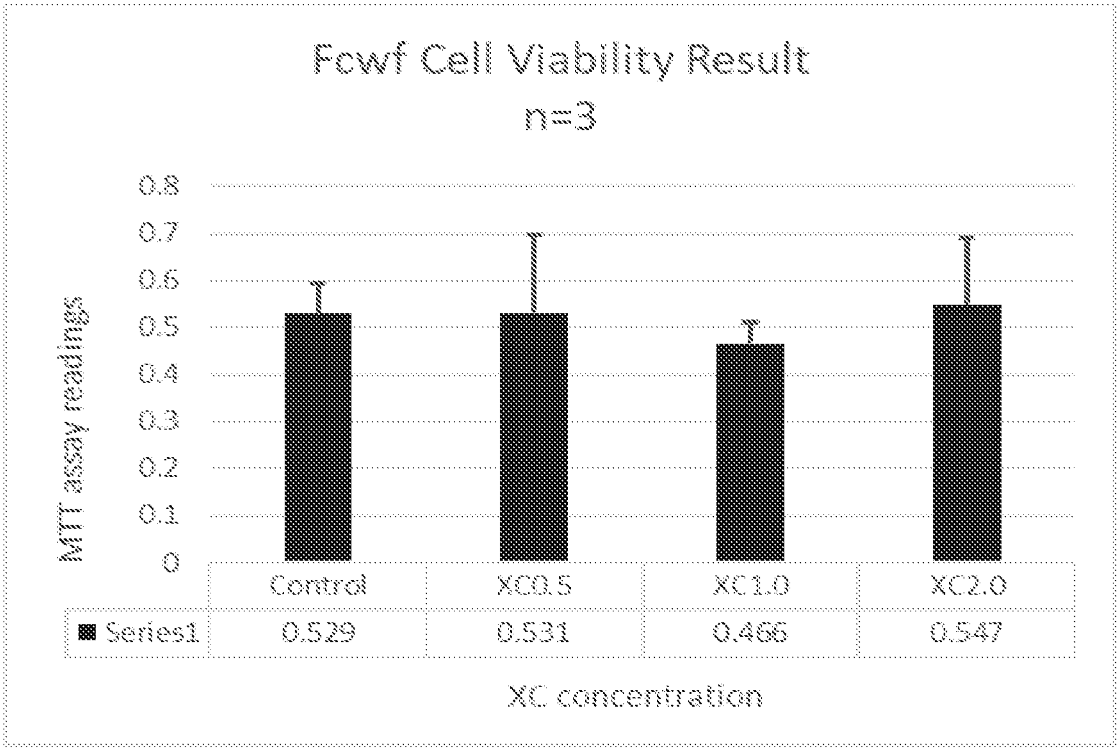
FIG. 1 is a bar graph showing cell viability of Fcwf cells incubated with various concentrations of XC extract. The X axis represents XC extract concentration and the Y axis represents MTT assay readings.

As used herein, the term "nutraceutical" refers to a pharmaceutical-grade and standardized nutrient, usually food or parts of food that confers health benefits. In the United States nutraceuticals are classified with dietary supplements and food additives. They can be categorized as dietary fiber, pre- and probiotics, polyunsaturated fatty acids, antioxidants, and other types of herbal and natural foods. Popular nutraceuticals include ginseng, Echinacea, green tea, glucosamine, omega-3, lutein, folic acid, and cod liver oil. Nutraceuticals are used for treating or preventing a number of diseases including arthritis, cold and cough, sleeping disorders, gastrointestinal diseases, certain cancers, osteoporosis, blood pressure, cholesterol control, pain killers, depression, and diabetes. Because nutraceuticals are naturally occurring foods or food parts, they confer fewer side effects and cost less than engineered pharmaceuticals.

As used herein, "botanical extract" refers to a concentrated solution made by extracting chemical constituents out of plant cellulose with solvent, usually a solution of alcohol and water or glycerin and water. Botanical extracts are used to maintain, restore, and improve health. As used herein, "herbal extracts" refer to a botanical extract wherein the plant is specifically an herb.

As used herein, the terms "bioactive" and "bioactive compound" refer to extra-nutritional components that are found in small quantities in foods and provide health benefits beyond the basic nutritional value of the food. Exemplary bioactive compounds include but are not limited to carotenoids, caritine, choline, coenzyme Q, dithiolthiones, flavonoids, phytosterols, phytoestrogens, glucosinolates, polyphenols, and taurine. Bioactive compounds have many beneficial properties including but not limited to antioxidant, anticarcinogenic, anti-inflammatory, and anti-microbial properties.

As used herein, "*Fagopyrum*" refers to a Genus of flowering plants of the family Polygonaceae, also referred to as the Buckwheat family.

As used herein, "*Fagopyrum dibotyo* (D. Don) Hara", "*Fagopyrum cymosum* (Trev) Meisn", and "the extract" can be used interchangeably and refer to the disclosed nutraceutical composition. *F. dibotyo* is a perennial herb with edible seeds and leaves that are rich in rutin. Other names for *Fagopyrum dibotyo* (D. Don) Hara include buckwheat, *Fagopyrum esculentum, Fagopyrum leptopodum, Fagopyrum acutatum* (Lehmann), and *Fagopyrum megaspartanium.*

As used herein, "ascites" refers to the abnormal buildup of fluid in the abdomen that is usually caused by liver cirrhosis.

As used herein, "liver function test" refer to a group of blood tests that give information on the state of a patient's liver. Inflamed or injured liver cells leak high amounts of liver enzymes into the bloodstream. These elevated liver enzymes can be detected with blood tests. Commonly elevated liver enzymes include but are not limited to Alanine transaminase (ALT), Aspartate transaminase (AST), Alkaline phosphatase (ALP), and Gamma glutamyl transpeptidase (γ-GT).

As used herein, "liver fibrosis" and "fibrosis" can be used interchangeably and refer to scarring of the liver due to conditions of untreated inflammation of the liver.

As used herein, "liver cirrhosis" and "cirrhosis" can be used interchangeably and refer to late stage, irreversible scarring of the liver. Cirrhosis can lead to liver failure and liver cancer if not treated.

Liver inflammation or injury can occur due to viral infection of the liver. Viruses that infect the liver include but are not limited to hepatitis A, hepatitis B, hepatitis C, hepatitis D, and hepatitis E.

As used herein, the terms "treat", "treating", "treatment" and "therapeutic use" refer to the elimination, reduction, or amelioration of one or more symptoms of a disease or disorder.

As used herein, the term "prophylactic agent" refers to an agent that can be used in the treatment of a disorder or disease prior to the detection of any symptom of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "effective amount" and "therapeutically effective amount" refer to the amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the terms "individual," "subject," and "patient" are used interchangeably, and refer to a mammal, including, but not limited to, humans, rodents, such as mice and rats, and other laboratory animals.

II. Compositions

Nutraceutical compositions including an effective amount of extract of *Fagopyrum dibotyo* (D. Don) Hara to inhibit viruses that affect the liver are provided. The disclosed compositions are useful in the treatment of liver disease or conditions, including but not limited to liver disease caused by viruses, parasites, alcohol, or bacteria.

A. *Fagopyrum dibotyo* Compositions

One embodiment provides compositions of extracts of *Fagopyrum dibotyo*. In one embodiment, the composition includes between 0.1 mg to 10 g of *F. dibotyo* extract. In some embodiments the compositions include 0.1 mg, 0.5 mg, 1 mg, 5 mg, 10 mg, 20 mg, 30 mg, 40 mg, 50 mg, 60 mg, 70 mg, 80 mg, 90 mg, 100 mg, 500 mg, 1 g, 5 g, or 10 g of *Fagopyrum dibotyo* extract. The preferred dose of extract (100:1) is 1.5 grams/day in dry form (pills or capsules). Oral formulation may include starch and other regular inactive ingredients. If only the active ingredient is considered, the preferred dose is 75 mg/day.

In some embodiments, the *F. dibotyo* extract is obtained from the roots of the plant. In another embodiment, the extract is obtained from the seeds of the plant. In yet another embodiment, the extract is obtained from the leaves of the plant or the flowers of the plant.

B. Active Components i. Flavonoid Compositions

In some embodiments, the active component of the *F. dibotyo* extract is 5,7,3',4'-tetrahydroxyflavan-3-ol $C_4$-$C_8$ dimers. 5,7,3',4'-tetrahydroxyflavan-3-ol is a flavan-3-ol, a major subclass of flavonoid present in many plants. Flavonoids, including flavan-3-ols, have antioxidant, anticarcinogenic, cardiopreventative, antimicrobial, anti-viral, and neuroprotective properties.

In one embodiment, the composition includes 0.001% to 50% of 5,7,3',4'-tetrahydroxyflavan-3-ol $C_4$-$C_8$ dimers. In some embodiments, the composition includes 0.001%, 0.01%, 0.1%, 1%, 5%, 10%, 20%, 30%, 35%, 40%, 45%, or 50% of 5,7,3',4'-tetrahydroxyflavan-3-ol $C_4$-$C_8$ dimers. The preferred dose of 5,7,3',4'-tetrahydroxyflavan-3-ol $C_4$-$C_8$ dimers is 30 mg (20% of the extract).

In another embodiment, the composition includes 0.001% to 50% of derivatives of 5,7,3',4'-tetrahydroxyflavan-3-ol $C_4$-$C_8$ dimers. In one embodiment, the derivatives are dimeric procyanidins aglycone. In some embodiments, the composition includes 0.001%, 0.01%, 0.1%, 1%, 5%, 10%, 20%, 30%, 35%, 40%, 45%, or 50% of derivatives of 5,7,3',4'-tetrahydroxyflavan-3-ol $C_4$-$C_8$ dimers. Other beneficial flavan-3-ols can be combined with compositions of extracts of *Fagopyrum dibotyo* including but not limited to catechin, epicatechin gallate, epigallocatechin, epigallocatechin gallate, proanthocyanidins, theaflavins, and thearubigins.

ii. Other Active Agent

Another embodiment provides a second active agent of *F. dibotyo* extract. The second active agent is Haike sapogenin. Sapogenins are the aglycones, or non-saccharide, portions of the family of natural products known as saponins. They are found in the tubers of various plants. In one embodiment, Haike sapogenin has activity against hepatitis virus.

In another embodiment, the *F. dibotyo* extract contains an effective amount of Haike sapogenin. The preferred dose for sapogenin is 15 mg/day.

C. Herbal Compounds

The disclosed nutraceutical compositions of *Fagopyrum dibotyo* extract can be combined with an herbal compound or molecule.

In one embodiment, the *F. dibotyo* nutraceutical contains green tea extract. The compositions can include 100-750 mg of green tea extract. In one embodiment, the preferred dose of green tea extract is 100 mg/day. In another embodiment, the *F. dibotyo* nutraceutical contains synthetic catechins or polyphenols.

In some embodiments, the *F. dibotyo* nutraceutical contains milk thistle extract. Silymarin is a flavonoid found in milk thistle and is believed to have antioxidant properties. The compositions can include 140 mg-200 mg milk thistle extract per dose. The preferred dose of milk thistle extract is 150 mg/day. In another embodiment the *F. dibotyo* nutraceutical can include synthetic silymarin.

In another embodiment, the *F. dibotyo* nutraceutical is combined with *Semen cassia* extract. The compositions can include 0.1 g to 15 g of *Semen cassia*. The preferred dose of *Semen cassia* extract is 1 g per day. In another embodiment, the *F. dibotyo* nutraceutical is combined with *Spica prunellae* extract. The composition can include 0.1 g to 15 g of *Spica prunellae* extract. The preferred dose of *Spica prunellae* extract is 1 g per day.

In some embodiments, the *F. dibotyo* nutraceutical composition includes compounds from *Radix* or *Forsythia. Radix angelicae pubescentis* and *Forsythia suspense* are believed to have anti-inflammatory properties. The composition can include 0.1 g to 15 g of compounds from *Radix* or *Forsythia*. The preferred dose of compounds from *Radix* or *Forsythia* is 1 g per day.

In one embodiment, the nutraceutical composition includes compounds from *Plantago depressa* Wild or *Taraxacum mongolicum* Hand-Mazz. Extracts from these herbs are commonly used as anti-ascites agents. The compositions can include 0.1 g to 15 g of compounds from *Plantago depressa* Wild or *Taraxacum mongolicum* Hand-Mazz. The preferred dose of compounds from *Plantago depressa* or *Taraxacum mongolicum* is 1 g per day.

In another embodiment, the nutraceutical composition includes compounds from *Thlaspi arvense* Linn., Tai Zi Shen (*Pseudostellaria heterophylla*), or *Poria* (*Wolfporia cocos*). The compositions can contain 0.1 g to 30 g of compounds from *Thlaspi arvense* Linn., Tai Zi Shen (*Pseudostellaria heterophylla*), or *Poria* (*Wolfporia cocos*). The preferred dose of compounds from *Thlaspi arvense* Linn., Tai Zi Shen (*Pseudostellaria heterophylla*), or *Poria* (*Wolfporia cocos*) is 1 g per day.

In one embodiment, the nutraceutical composition includes compounds from *Artemis cappalliris* Thunb. *Artemis cappalliris* is an herb with therapeutic effects for liver disease that is commonly used as an alternative therapy to pharmaceuticals. The compositions can include 0.1 g to 30 g of compounds from *Artemis cappalliris* Thunb. The preferred dose of compounds from *Artemis cappalliris* Thunb is 1 g per day.

D. Nutraceutical Compositions

Pharmaceutical compositions containing the *Fagopyrum dibotyo* extract can be formulated for administration by parenteral routes and can be formulated in dosage forms appropriate for each route of administration. The preferable route of delivery for the nutraceutical composition is orally.

The compositions disclosed herein can be administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed *F. dibotyo* nutraceutical compositions, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed *F. dibotyo* nutraceutical composition, generally dosage levels of 0.1 mg to 10 g are administered to mammals. The preferred dose of *F. dibotyo* extract is 150 mg per day.

i. Formulations for Oral Administration

In some embodiments the compositions are formulated for oral delivery. Oral solid dosage forms are described generally in Remington's Pharmaceutical Sciences, 18th Ed. 1990 (Mack Publishing Co. Easton Pa.

18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712, which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the *F. dibotyo* nutraceutical composition and inert ingredients which protect the composition in the stomach environment, and release of the biologically active material in the intestine.

In some embodiments, the nutraceutical compositions are formulated in capsules or tablets. The capsules or tablets can contain ground or powdered raw herbs or plants, or dried extract. The nutraceutical compositions can be formulated as a once-daily supplement, a twice daily supplement, or a three times daily supplement.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

In another embodiment, the *F. dibotyo* nutraceutical composition is administered in the form of a whole herb tea. Ground or powdered dried raw herbs or dried powdered extract are processed in a manner such that the extract is released into the boiling water during preparation of the tea.

III. Methods of Manufacture

Methods of making medicinal plant extracts are well known in the art. Extraction involves removing the medicinally active portion of the plant from the inert components using selective solvents in standard extraction procedures. Plant and herb extracts vary in the solvent used for extraction, temperature, and extraction time. Types of extracts include but are not limited to alcoholic extracts (tinctures), vinegars (acetic acid extracts), hot water extract (tisanes), long-term boiled extract, decoctions, and cold infusion of plants (macerates). Exemplary extraction procedures include but are not limited to maceration, infusion, digestion, decoction, percolation, hot continuous extraction (Soxhlet), aqueous alcohol extraction by fermentation, counter-current extraction, and ultrasound extraction (sonication). The extract obtained from the plant is relatively impure liquid that can be used in the form of tinctures and fluid extracts without additional processing. However, the extract can be processed further to be incorporated into other dosage forms such as tablets or capsules.

A. Maceration

In one embodiment, the *F. dibotyo* extract can be prepared using maceration technique of extraction. In this method, the whole or coarsely powdered plant is placed in a stoppered container with a solvent and allowed to stand at room temperature for at least 3 days with frequent agitation until the soluble matter has dissolved. Common solvents that are used to extract bioactive compounds from plants include but are not limited to water, ethanol, methanol, chloroform, ether, and acetone. The mixture is strained, the solid material is pressed, and the combined liquids are clarified by filtration or decantation after standing. Infusions can be prepared by macerating the whole plants for a short period of time with cold or boiling liquid. Infusions are dilute solutions of the readily soluble portions of the whole plant. Digestion is a form of maceration in which low heat is used during the process of extraction. This increases the solvent efficiency.

B. Hot Continuous Extraction

Plant extracts can be obtained through hot continuous extraction (Soxhlet). Generally, a small amount of dry sample is placed in a thimble. The thimble is then placed in a distillation flask which contains a solvent appropriate for extracting the bioactive of interest. When the liquid content reached the siphon arm, the liquid is emptied into the bottom of the flask. This solution carries extracted solutes into the bulk liquid. The solute remains in the distillation flask and the solvent passes back to the sample in the thimble. The process runs repeatedly until the extraction is completed.

C. Aqueous Alcohol Extraction by Fermentation

In one embodiment, the herb and plant extracts of the nutraceutical compositions disclosed herein can be produced through aqueous alcohol extraction. This method involves soaking the plant material in solvent for a specified period of time during which it undergoes fermentation. The generation of alcohol in situ facilitates the extraction of the bioactives contained in the plant material.

D. Ultrasound-Assisted Extraction

In one embodiment, the botanical extracts can be obtained through ultrasound assisted extraction (UAE) methods. UAE is a non-conventional mode of extracting bioactives from plants and herbs. In this method, ultrasound waves ranging from 20 kHz to 2000 kHz are pulsed through the intact tissue of the plant or herb. The ultrasound energy causes organic and inorganic materials to leach out of the plant material and into the solvent that the plant is contained within.

E. Enzyme-Assisted Extraction

In another embodiment, the extracts can be obtained through enzyme-assisted extraction. In this method, plants are pre-treated with specific enzymes to facilitate extraction of compounds that are retained in polysaccharides and lipid bodies within the cell wall. Exemplary enzymes include but are not limited to cellulase, α-amylase, and pectinase.

F. Microwave-Assisted Extraction

In some embodiments, botanical extracts are prepared through the method of microwave-assisted extraction (MAE). This method involves extracting soluble products into a fluid form using microwave energy and was first described by Alupului (*U.P.B. Sci. Bull.*, Series B, 74:129-142 (2012)). Microwave energy disrupts hydrogen bonding between molecules, enhancing the migration of dissolved ions out of the plant matrix while also promoting solvent penetration into the plant matrix.

IV. Methods of Use

Nutraceutical compositions and their use thereof to increase or improve liver function or to treat liver disease are disclosed herein. In one embodiment, the *Fagopyrum dibotyo* nutraceuticals are useful in treating liver diseases associated with hepatitis virus infection.

A. Hepatitis Virus Infection

In some embodiments, the disclosed nutraceutical compositions can inhibit viral hepatitis. The viral hepatitis can be hepatitis A, hepatitis B, or hepatitis C. Inhibition of viral hepatitis can occur through but are not limited to the following, inhibition of viral entry and attachment, inhibition of viral replication, or interfering with the viral capsid.

The disclosed nutraceutical compositions can also be used in late-stage patients who are beyond traditional drug treatment. Late-stage patients who are administered the disclosed nutraceutical compositions can recover from viral-induced hepatitis virus. In some embodiments the disclosed nutraceutical compositions can be used for the management of viral-induced late stage hepatitis.

The disclosed nutraceutical compositions can also be used independently or in conjunction with other therapeutics to inactivate hepatitis virus A and hepatitis virus C.

B. Improved Liver Function

In some embodiments, the disclosed nutraceutical compositions can reduce symptoms of liver disease including ascites, elevated serum levels of liver enzymes, liver fibrosis, and liver cirrhosis. Without being bound to any one theory, it is believed that the disclosed nutraceutical compositions can reduce inflammation in the liver, thus reducing symptoms of liver diseases. In one embodiment, the antioxidant properties of 5,7,3',4'-tetrahydroxyflavan-3-ol $C_4$-$C_8$ dimers can reduce inflammation in damaged or infected liver. Flavan-3-ols have been shown to behave as antioxidants via several mechanisms including the scavenging of free radicals. The generation of free radicals can cause oxidative damage to DNA, lipids, and proteins, which if left unchecked can lead to disease progression. In one embodiment, the disclosed nutraceutical compositions can act as antioxidants to reduce levels of free radicals and subsequent inflammation.

The disclosed *F. dibotyo* nutraceutical compositions can be administered to a subject in need thereof to improve or increase liver function. In some embodiments, the subject in need thereof has elevated serum liver enzymes. Damaged hepatocytes leak liver enzymes into the blood stream; therefore measuring liver enzymes in the blood can detect liver damage. Exemplary serum liver enzymes indicative of poor liver function include but are not limited to aspartate aminotransferase (AST), alanine aminotransferase (ALT), alkaline phosphatase (ALP), and gamma-glutamyl transferase (GGT). In a liver enzyme test, blood is drawn from the subject and the serum is collected. The lab then measures levels of the diagnostic liver enzymes within the serum fraction of the blood.

While the normal serum levels of liver enzymes range between different labs, the average ranges are as follows: normal serum levels of AST range from 10-40 units per liter of serum, normal serum levels of ALT rage from 7-55 units per liter of serum, normal serum levels of ALP range from 45-115 units per liter of serum, and normal serum levels of GGT range from 9-48 units per liter of serum. ALT and AST levels over 1000 units/liter indicate liver damage due to viral hepatitis. AST levels that are higher than ALT levels indicate liver damage due to cirrhosis, alcohol, or drugs. ALP and GGT levels 2-5 times the normal level are indicative of liver damage or disease.

In one embodiment, a subject is administered a liver enzyme test and the results show elevated liver enzymes. The subject is then administered an effective amount of *F. dibotyo* nutraceutical for 7, 14, 21, 28, 35, 48, 90, 120, or 150 days, and the liver enzymes are re-measured. The subject can be administered the nutraceutical composition until an improvement in liver enzyme levels is observed.

Another embodiment provides *F. dibotyo* nutraceutical compositions that decrease liver enzyme levels and bring them within the normal range. One embodiment provides *F. dibotyo* nutraceutical compositions that cause 30%, 40%, 50%, 55%, 60%, 65%, 70%, 75%, 80%, 85%, 90%, 95%, 98%, 99%, or 100% improvement in liver enzyme levels.

C. Additional Methods of Use

In one embodiment, *F. dibotyo* nutraceutical compositions can have a diuretic effect and treat ascites in subjects in need thereof.

In another embodiment, the disclosed nutraceutical compositions can be used to treat or prophylactically prevent cancer. In one embodiment, the cancer is hepatic cancer. In another embodiment, the hepatic cancer is caused by hepatitis virus infection. Without being bound by any one theory, it is believed that the anti-tumor properties of *Fagopyrum* species can be attributed to phenolic compounds in extracts from the plant (Jing, et al., *Int J Mol Sci,* 17:589 (2016)). *Fagopyrum* species have strong anti-proliferative and pro-apoptotic effect on tumors both in vitro and in vivo (PK Chan, *Life Sci,* 72: 1851-1858 (2003)).

V. Combination Therapies

The disclosed nutraceutical compositions can be administered to a subject in need thereof alone or in combination with one or more additional therapeutic agents. In some embodiments, the nutraceutical composition and the additional therapeutic agent are administered separately, but simultaneously. The nutraceutical composition and the additional therapeutic agent can also be administered as part of the same composition. In other embodiments, the nutraceutical composition and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The nutraceutical composition can be the first or the second therapeutic agent.

The nutraceutical composition and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the nutraceutical composition can be co-administered with one or more additional agents that function to enhance or promote an immune response or reduce or inhibit an immune response.

A. Anti-Inflammatory Agents

In one embodiment, the disclosed *F. dibotyo* nutraceutical compositions also contain an anti-inflammatory agent. The anti-inflammatory agents can be herbal compounds such as *Radix* and *Forsythia*. Other exemplary herbs commonly used to reduce inflammation include but are not limited to *Forsythia suspense, Radix isatidis, Pulsatilla radix, Scutellaria baicalensis, Coptis chinesesis, Flos lonicerae, Isatidis folium, Viola yedoensis, Houttuynia, cordato*, and *Patrinia herba.*

In other embodiments, the anti-inflammatory agents are pharmaceutical agents. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

B. Chemotherapeutic Agents

In one embodiment, the disclosed *F. dibotyo* nutraceutical compositions can be combined with one or more chemotherapeutic agents. The chemotherapeutic agent can be an herbal compound. Exemplary herbs commonly used for anti-cancer effects include but are not limited to extract of *Hedyotis Diffuse* Willd, extract from *Sephora Flavescent* Ait., *Trillium tschonoskii* Maxim., *Rhizma Curcuma, Salvia miltiorrhiza, Evodia ruaecarpa, Carthami Flos, Scutellaria barbata*, Pien Tze Huang, *Alocasia cucullata, Ganoderma lucidum, Sinapisalba, Atractylodes macrocephala, Coix*

*lacryma-jobi, Polyporus adusta, Radix Astragalus, Radix Adenophorae, Radix Ophiopogonis, Radix glycyrrhizae, Poria* and *Oldenlandia diffusa.*

The chemotherapeutic agent can also be a pharmaceutical agent. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof.

C. Liver-Protective Therapeutics

In some embodiments, the disclosed *F. dibotyo* nutraceutical compositions can be combined with liver-protective agents. The liver protective agent can be an herbal extract. Exemplary liver protective herbal extracts include but are not limited to *Artemesia capillaris* Thunb. *Buplerum chinense* DC, rhizome of Chinese goldthread, *Poria cocos* Tuckahoe, *Pinellia ternate, Scutellaria baicalensis* Georgi, *Agaric umbellate*, pore fungus, ginseng, *Phellodendri Cortex*, Largehead atractylodes, *Scutellaria baicalensis* Georgi, *Gardeniae Fructus*, Cassia twigs, *ramulus cinnamomi, Glycyrrhizae Radix, Alisma orientalis* Sam., ginger, and *Artemisiae scopariae* Herba.

In other embodiments, the liver protective agents are pharmaceutical agents. Exemplary liver protective drugs include but are not limited to colchicine, corticosteroids, curcumin, glycyrrhizin, interferons, Liv 52, nitric oxide, resveratrol, silymarin, sulfoadenosylmethionine, and thalidomide.

D. Diuretics

A common symptom of liver disease is ascites, or the retention of fluid in the abdominal cavity. In some embodiments, the disclosed *F. dibotyo* nutraceutical compositions can be combined with diuretics. The diuretics can be herbal extracts. Exemplary herbal diuretics include but are not limited to *Plantago depressa* Wild and *Taraxacum mongolicum* Hand-Mazz.

In another embodiment, the diuretic is a pharmaceutical agent. Exemplary diuretics include but are not limited to spironolactone, furosemide, amiloride, metolazone, and mannitol.

E. Anti-Viral Therapeutics

In some embodiments, the disclosed *F. dibotyo* nutraceuticals can be combined with anti-viral hepatitis treatments. Exemplary anti-viral drugs for HBV include lamivudine and adefovir dipivoxil. Exemplary treatment for HCV include but are not limited to a combination of peginterferon and ribovarin, and Direct acting antiviral (DAA) agents such as elbasvir/grazoprevir, sofosbuvir/velpatasvir, and ombitasvir/paritaprevir/ritonavir/dasabuvir.

EXAMPLES

Example 1: XC Extract does not Impact Cell Viability

Materials and Methods

To determine if *Fagopyrum dibotyo* extract (XC extract) is associated with cytotoxicity, XC extract was dissolved in either MEM or DMEM for FCV F9 or HAV viral infections in Fcwf or FRhK cells, respectively. Fcwf and FRhK cells were grown in 96 well plate until confluent. XC extract in MEM was added to the wells at 0, 0.1, 1, and 2%, followed by incubation overnight. MTT assay was performed on the cells and cell viability was calculated.

Figure 2:
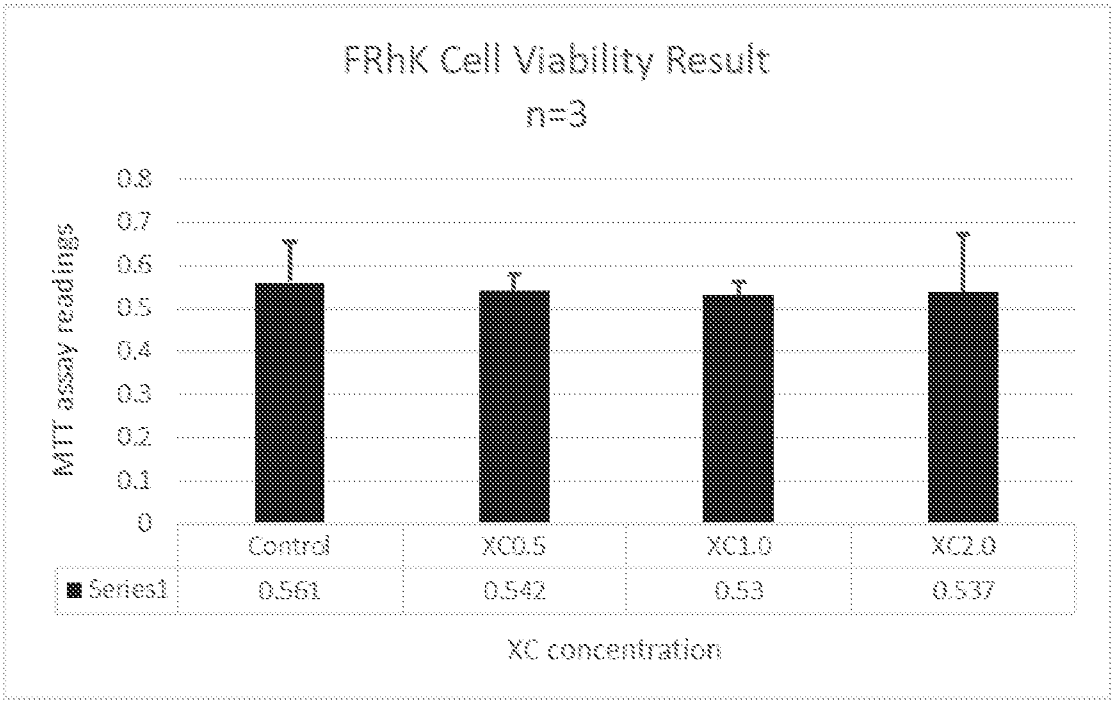
FIG. 2 is a bar graph showing cell viability of FRhK cells incubated with various concentrations of XC extract. The X axis represents XC extract concentration and the Y axis represents MTT assay readings.
Figure 3:
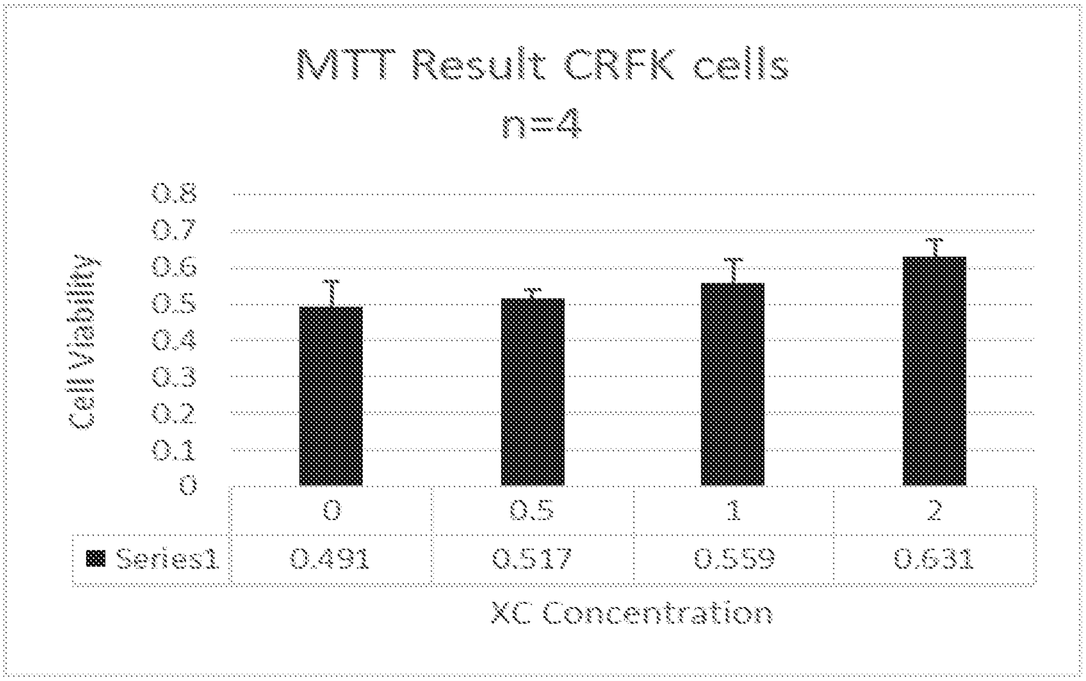
FIG. 3 is a bar graph showing cell viability of CRFK cells incubated with various concentrations of XC extract. The X axis represents XC extract concentration and the Y axis represents MTT assay readings.

Results:

XC extract did not reduce cell viability in Fwcf or FRhK cells even at 2% concentration (FIG. 1, FIG. 2, and FIG. 3). Statistical analysis was performed using one way ANOVA and t-test. The results demonstrate that there is no significant difference among all samples tested. That is, XC extract up to 2% does not impact cell viability in Fcwf or FRhK cells.

FIG. 3 shows that XC extract did not reduce cell viability in CRFK cells even at 2% concentration. Statistical analysis was performed using one way ANOVA and t-test. The results demonstrate that there is a significant difference among all samples tested (ANOVA $p=0.015$). Result from t test indicates that the only differences among samples are between 2% and control (0%), and 2% and 0.5% ($p<0.05$). That is, XC extract at 2% concentration significantly increased cell viability in CRFK cells.

The above results demonstrate that XC extract is not cytotoxic if the concentration is below 2%.

Example 2: Pre-Treatment with XC Extract Reduces Viral Infection

Materials and Methods:

FRhK cells were pretreated with different concentrations of XC for 1 hour before TCID50 assay. FRhK cells were plated in 96-well tissue culture plates in DMEM culture medium with 10% fetal bovine serum and antibiotics at 35 degrees, 5% $CO_2$. When cells covered the surface of each well to >90%, XC extract dissolved in serum free DMEM culture medium (filtered) were added at 0, 0.1%, 0.2% and 1%, followed by incubation for 1 h. XC medium was removed and HAV was added at different dilution concentrations from $10^{-3}$ to $10^{-5}$, after 1 h absorption, virus was removed and DMEM medium with 2% fetal bovine serum (FBS) was added to each well. Results were recorded and calculated after 8 days.

Figure 4:
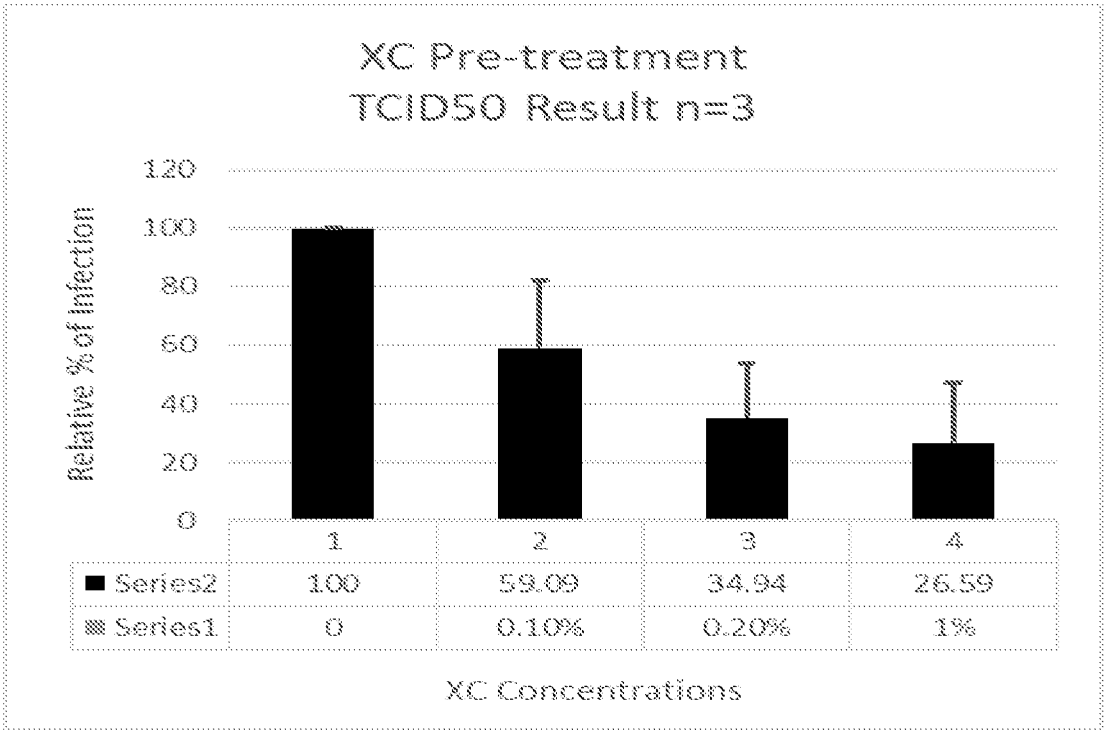
FIG. 4 is a bar graph showing HAV infection in FRhK cells pre-incubated with various concentrations of XC extract. The X axis represents XC concentration and the Y axis represents relative percent of infection.

Results:

FIG. 4 shows results from 3 independent experiments that indicate a significant inhibition of viral infection at all concentrations of XC extract, even though there was no direct contact of XC extract and virus. Statistical analysis shows that XC extract at all concentrations significantly reduced HAV infection rate in FRhK cells ($n=3$, $p<0.05$). At 1%, pre-incubation of XC extract with FRhK cells for 1 h reduced HAV infection rate to 26.59%. On the other hand, there is no statistical difference among the concentrations on the effect of HAV ($p=0.23$, $p=0.14$, $p=0.63$). The result indicates that XC extract is effective in reducing HAV infection of FRhK cells if XC extract is incubated with FRhK cells prior to HAV infection, and the apparent dose response is statistically insignificant. Results from one way ANOVA show that there is no difference among XC concentrations ($p=0.619$)

Example 3: Viral Incubation with XC Extract Reduces Viral Infection

Materials and Methods:

FRhK cells were plated in 96-well plate as described above. XC at 0.1%, 0.2%, and 1% were mixed with HAV at different dilutions shown above. The mix was removed after 1 hour absorption, and the mix was replaced with DMEM medium with 2% FBS. Result was recorded and calculated after 8 days.

Figure 5:
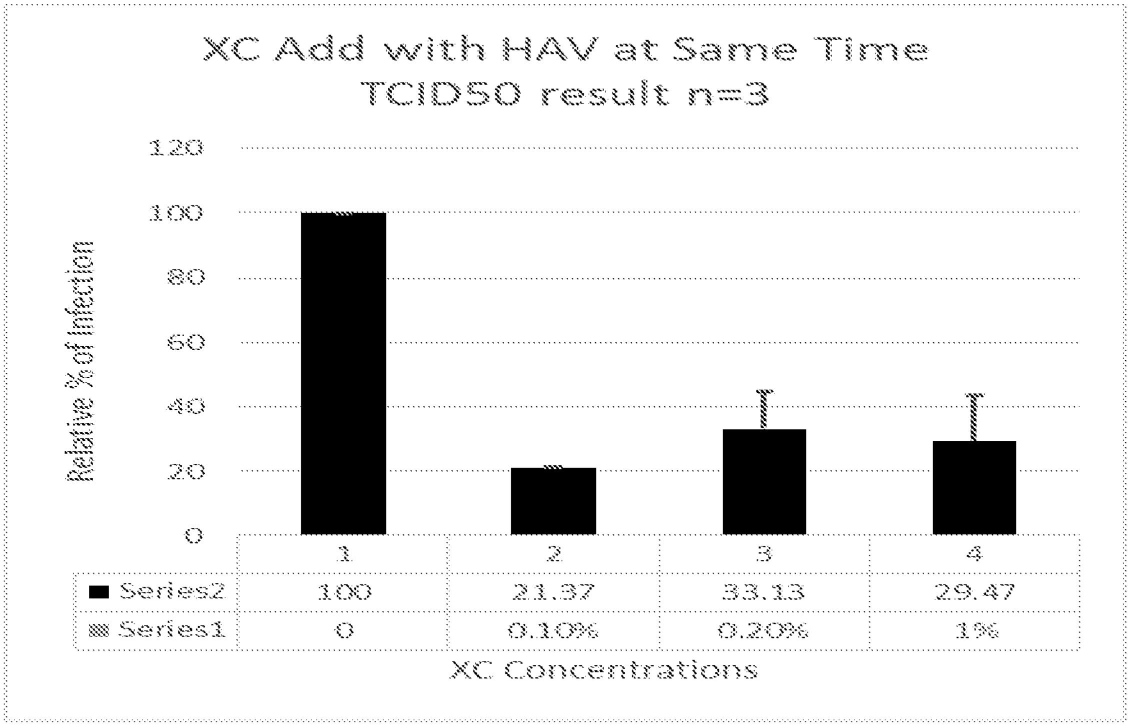
FIG. 5 is a bar graph showing HAV infection in FRhK cells incubated with various concentrations of XC extract. The X axis represents XC concentration and the Y axis represents relative percent of infection.

Results:

FIG. 5 shows that XC at all concentrations significantly inhibited F9 viral infection in CRFK cells. Data was obtained from 3 independent experiments. Results from one way ANOVA test shows a significant difference is present among 3 concentrations of XC extract (p=0.005). Lower concentrations of XC extract have a higher efficacy than higher concentrations. Statistical analysis using t-test shows that XC extract at all concentrations significantly reduced HAV infection rate in FRhK cells (n=3, p<0.05). There is no statistical difference among the concentrations on the effect of HAV (p=0.15, p=0.37, p=0.74). The result indicates that XC extract is effective in reducing HAV infection of FRhK cells when XC extract was incubated with HAV and FRhK cells during HAV infection.

Example 4: XC Extract Can Reduce Infection Rate Without Contacting the Virus Itself Materials and Methods:

FRhK cells were cultured as described in Example 1. HAV was added to the wells at different dilutions and allowed to incubate for 1 h. HAV was removed and XC extract in serum free DMEM medium was added to the wells. The cells were allowed to grow for 8 days before result recording was performed.

Figure 6:
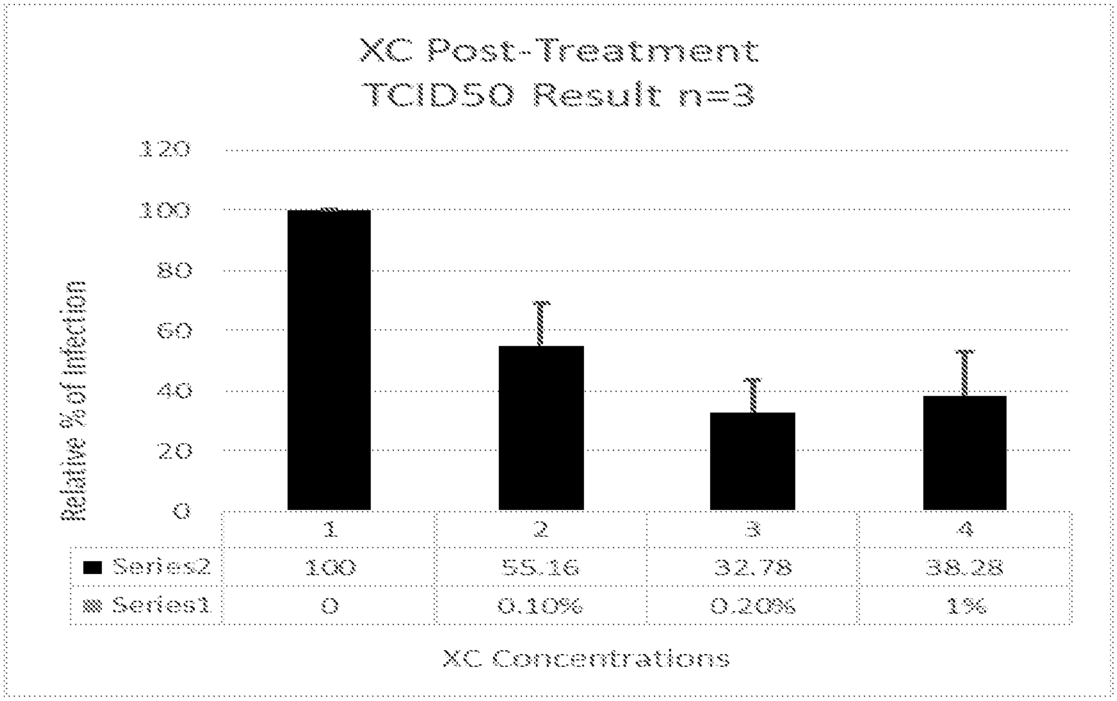
FIG. 6 is a bar graph showing HAV infection in FRhK cells infected with HAV before being treated with various concentrations of XC extract. The X axis represents XC concentration and the Y axis represents relative percent of infection.
Figure 7:
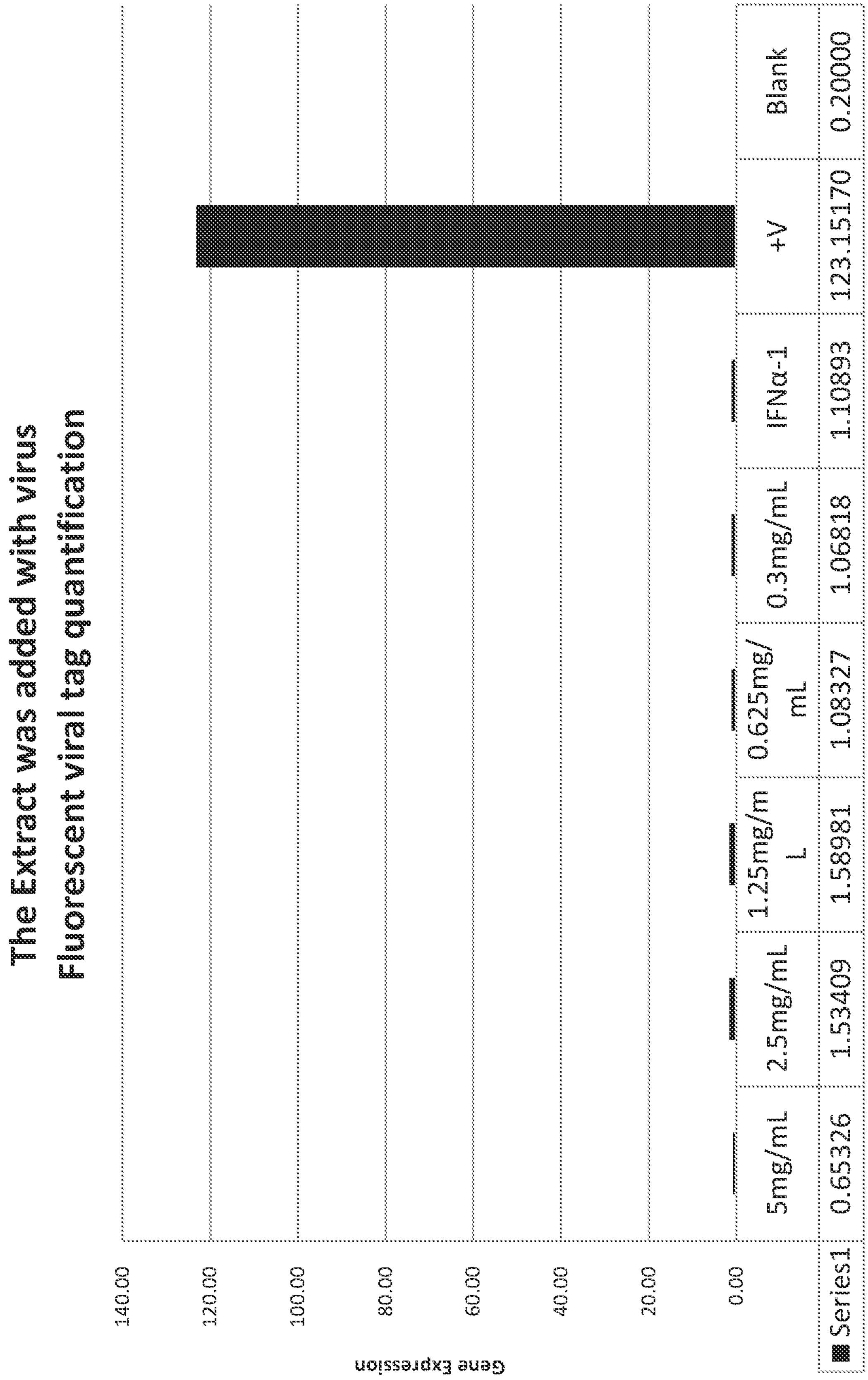
FIG. 7 is a bar graph showing expression of NS5B in Huh7.5.1 cells incubated with HCV and various concentrations of XC extract, IFNα-1, or virus only. The X axis represents experimental group and the Y axis represents gene expression level.
Figure 8:
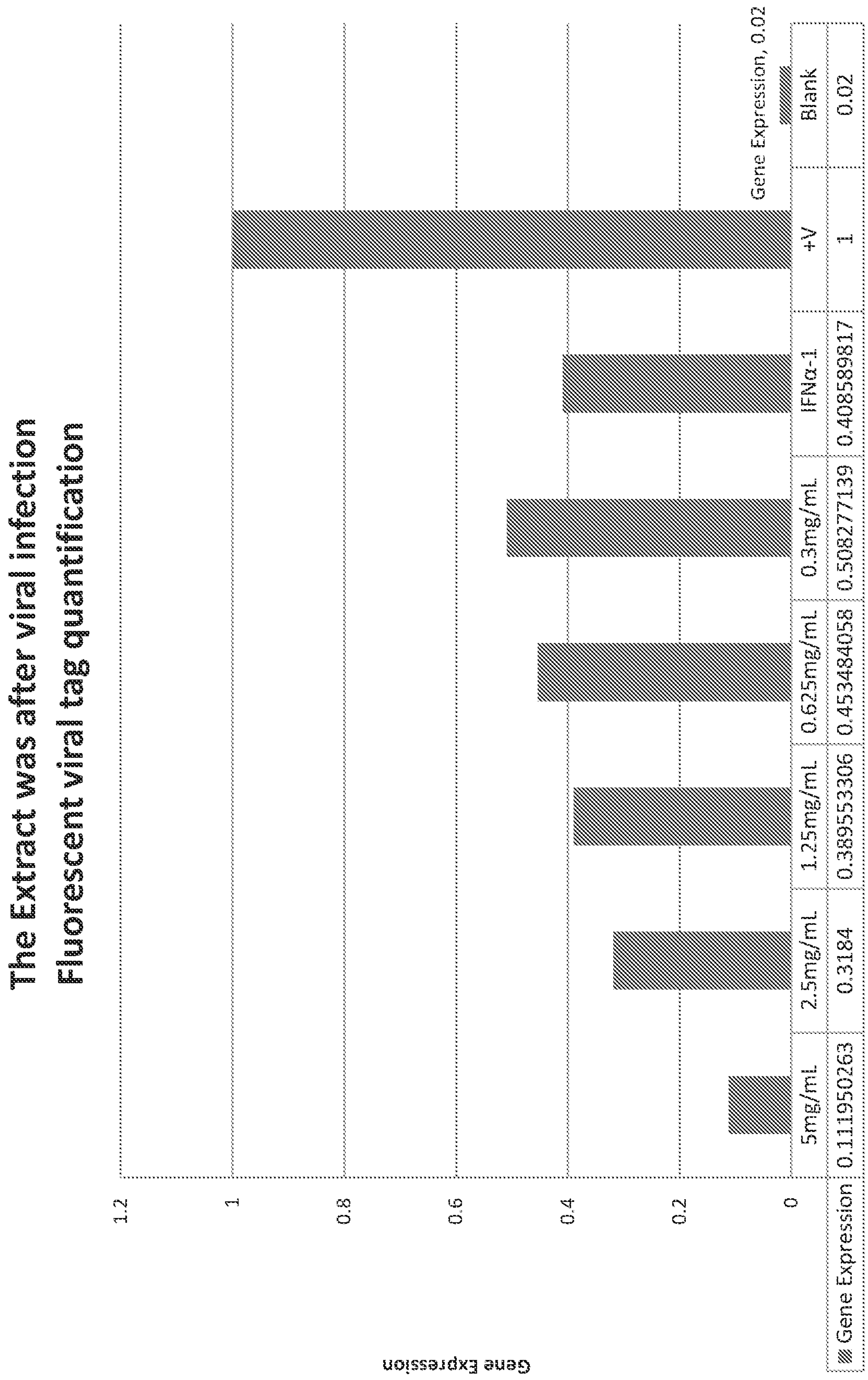
FIG. 8 is a bar graph showing expression of NS5B in HCV infected Huh7.5.1 cells incubated with various concentrations of XC extract, IFNα-1, or virus only. The X axis represents experimental group and the Y axis represents gene expression level.
Figure 9:
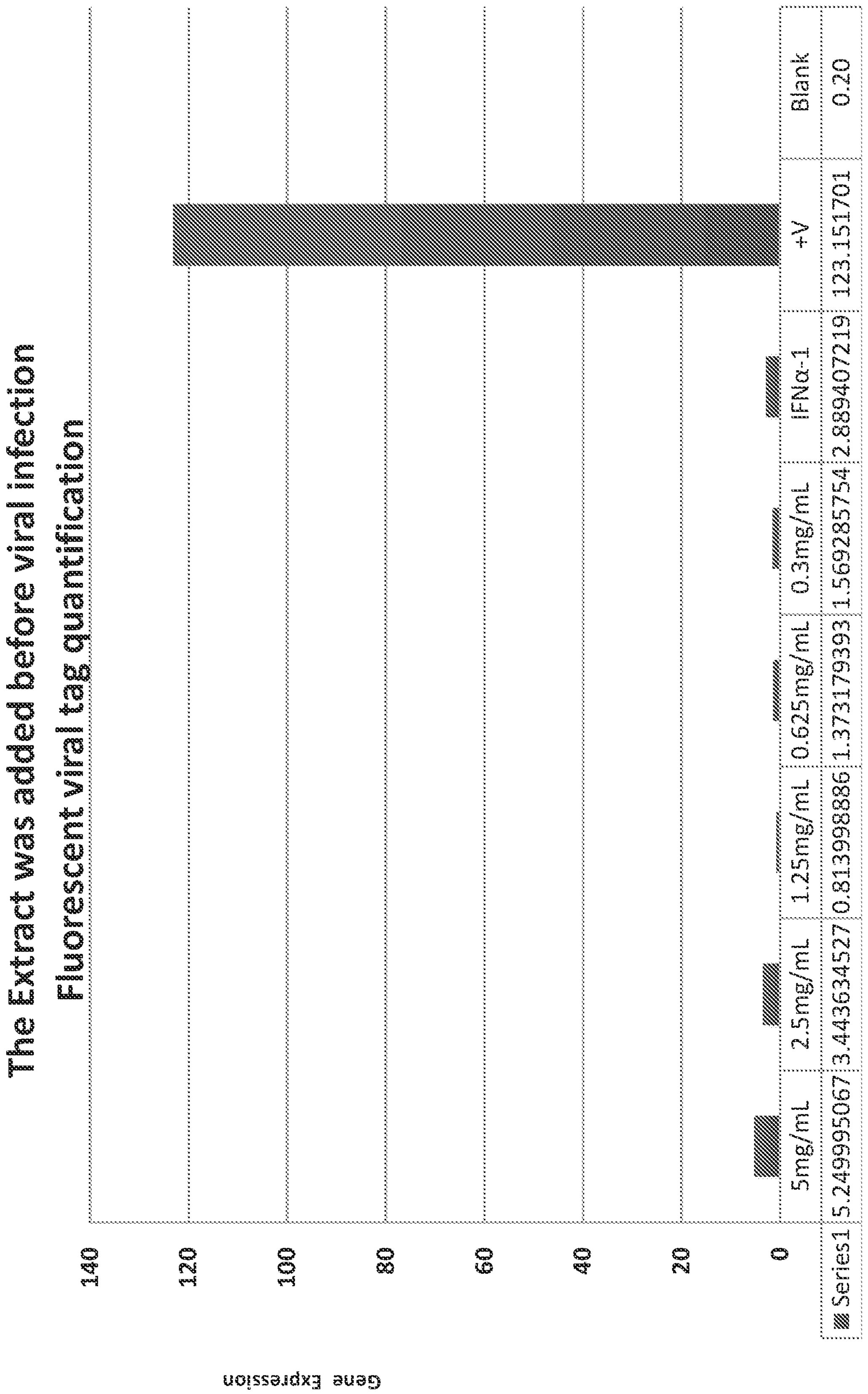
FIG. 9 is a bar graph showing expression of NS5B in Huh7.5.1 cells pre-treated with various concentrations of XC extract or IFNα-1, then infected with HCV. The X axis represents experimental group and the Y axis represents gene expression level.

Results:

FIG. 6 shows results from 3 independent experiments that show that without direct contact with the virus, XC extract at all concentrations significantly lowered HAV infection. Statistical analysis shows that XC extract at all concentrations significantly reduced HAV infection rate in FRhK cells (n=3, p<0.05). There is no statistical difference among the concentrations on the effect of HAV (p=0.097, p=0.22, p=0.63). The result indicates that XC extract is effective in reducing HAV infection of FRhK cells after HAV infection.

Result from one way ANOVA shows there is no difference among XC concentrations (p=0.693). In conclusion, HAV can be effectively inhibited by XC extract by different incubation methods. The methods limited the use of XC extract to just once and the results are statistically significant. HAV is one of the most difficult viruses to inactivate due to its size and non-enveloped structure similar to poliovirus and feline calicivirus. Thus, XC is a strong inhibitor of HAV.

Example 5: XC Extract Inhibits HCV Infection Similarly to IFN-α

Materials and Methods:

Huh7.5.1 cells were allowed to grow in 12 well plate until confluent. Cell culture medium containing 2% FBS was used to dilute XC extract before adding to the wells with 3 repeating per concentration. Positive control was IFN-α at 1000 U/ml. Negative control is adding virus only, and blank control were wells without any treatment. After 48 h incubation, cells were harvested and mRNA was extracted for PCR analysis of NS5B expression from HCV. The primers used are showing below:

```
                                    (SEQ ID NO: 1)
NS5B-F        5'>TCGTATGATACCCGATGCT<3'

                                    (SEQ ID NO: 2)
NS5B-R        5'>GTTTGACCCTTGCTGTTGA<3'
```

Real time PCR (RT-PCR) was performed according to the sequence of 1) 95° C. 5 min first cycle; 2) 95° C. 10 sec, 55° C. 30 sec, and 72° C. 30 sec as the next 40 cycles. The fluorescent intensity was recorded and the positive control (virus only) was set at 100%. All sample expression was calculated as % of control.

Results:

XC extract was added at the same time as HCV, incubated for 1 hour, washed with cell culture medium, and new cell culture medium was added and incubated for 48 hours prior to mRNA extraction. The result demonstrates that XC at all concentrations effectively inhibited HCV infection similar to the effect of 1000 U/ml IFN-α, a HCV drug.

XC extract was added after HCV infection of cells, incubated for 1 hour, washed with cell culture medium, and new cell culture medium was added and incubated for 48 hour prior to mRNA extraction. The results demonstrate that XC at all concentrations effectively inhibit HCV infection either similar to the effect of 1000 U/ml IFN-α, or better at 5 mg/ml.

XC extract was added to Huh7.5.1 cells, incubated for 1 hour, washed with cell culture medium, and added HCV to the well, followed by 1 hour incubation. The virus was then removed and new cell culture medium was added and incubated for 48 hours prior to mRNA extraction. The results demonstrate that XC at all concentrations effectively inhibit HCV infection similar to the effect of 1000 U/ml IFN-α.

In summary, XC extract is effective to inhibit HCV infection with prophylactic and treatment properties similar to IFN-α, a known biological drug to treat HCV.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

The invention claimed is:

1. A method of inhibiting viral hepatitis in a subject in need thereof, the method comprising the steps of: administering to the subject an effective amount of a composition comprising a therapeutically effective amount of an active component consisting of 5,7,3',4'-tetrahydroxyflavan-3-ol C4-C8 dimers and at least one excipient to inhibit viral hepatitis.

2. The method of claim 1, wherein the subject in need thereof has hepatitis A virus, hepatitis B virus, or hepatitis C virus.

3. The method of claim 1, wherein the subject in need thereof has viral-induced late stage hepatitis.

4. The method of claim 1, wherein the composition comprises 0.001% to 50% of 5,7,3',4'-tetrahydroxyflavan-3-ol C4-C8 dimers.

5. The method of claim 1, wherein the composition comprises 20 mg to 100 mg of 5,7,3',4'-tetrahydroxyflavan-3-ol C4-C8 dimers.

6. The method of claim 1, wherein the composition is administered orally.

* * * * *